United States Patent [19]
Holan et al.

[11] Patent Number: 4,753,960
[45] Date of Patent: Jun. 28, 1988

[54] OXIME INSECTICIDES

[75] Inventors: George Holan, Brighton; Kurt Rihs, West Footscray; Wynona M. P. Johnson, Bentleigh, all of Australia

[73] Assignee: Dunlena PTY. LTD., Australia

[21] Appl. No.: 847,903

[22] PCT Filed: Jul. 22, 1985

[86] PCT No.: PCT/AU85/00164
§ 371 Date: Mar. 10, 1986
§ 102(e) Date: Mar. 10, 1986

[87] PCT Pub. No.: WO86/00894
PCT Pub. Date: Feb. 13, 1986

[30] Foreign Application Priority Data

Jul. 31, 1984 [AU] Australia .............................. PG 6308

[51] Int. Cl.$^4$ ............................................. A61K 31/30
[52] U.S. Cl. .................................. 514/464; 514/640; 564/256; 549/442
[58] Field of Search ................ 564/256; 514/640, 464; 549/442

[56] References Cited

U.S. PATENT DOCUMENTS 4,079,149  3/1978  Henry .................................... 564/256
4,474,815  10/1984  Holan et al. ......................... 549/442

OTHER PUBLICATIONS

"Pyrethrum The Natural Insecticide", Casida (ed.), Ch. 10, pp. 195–210, Academic Press, NY, 1973.
"Naturally Occurring Insecticides", Jacobsen and Crosby, (eds.), Ch. 1, pp. 59–64, Marcel Dekker, Inc., NY 1971.
"Insecticides Action and Metabolism", O'Brien, pp. 167–168, Academic Press, NY 1967.

Primary Examiner—James H. Reamer
Attorney, Agent, or Firm—Bacon & Thomas

[57] ABSTRACT

Compounds with anthropodicidal activities having the general formula (1)

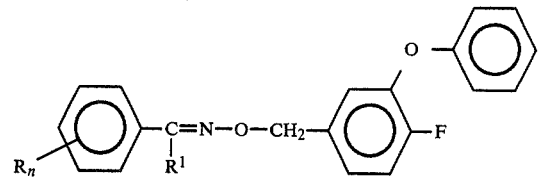

and their isomeric forms wherein R represents F, Cl, Br, ethoxy, methoxy or propxy and n is an integer between 1 and 5; or R represents 3,4-methylenedioxyl; and $R^{40}$ represents di- or trichloromethyl, fluorodichloromethyl or trifluoromethyl.

13 Claims, No Drawings

OXIME INSECTICIDES

The invention relates to new 4-fluorophenoxy-benzyl ethers of oximes of substituted phenyl halomethyl ketones, to a process for their preparation and to their use as arthropodicides, especially as insecticides and acaricides.

Reference has been made in the literature to a general class of alkyl aryl ketone oxime ethers of the general structure

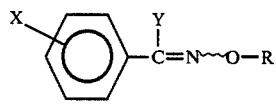

wherein X is one or more substituents, Y is an alkyl group and R-OH is the alcohol component of active pyrethroid esters (Michael J. Bull et al., *Pesticide Science*, 1980, 11, 249-256). The same reference discloses specifically a limited group of compounds falling within the broad class in which X is 4-chloro, 4-fluoro or 4-methoxy, Y is methyl, ethyl, isopropyl, cyclopropyl or cyclobutyl and R is 3-phenoxybenzyl. Some of these compounds showed insecticidal activity. U.S. Pat. No. 4,079,149 discloses a group of compounds of the same class in which the substituent X is one or two halogen atoms or alkyl or alkoxy groups and Y is inter alia an alkyl group of two or more carbon atoms, optionally substituted with one or more halogen atoms and R is 3-phenoxybenzyl U.K. Patent Application No. 2,025,407 discloses a similar group of compounds in which R is a 2,6-dihalobenzyl group. Neither of these references, however, discloses any specific compounds in which the group Y is a halogenated alkyl group.

The present invention provides new compounds of the general formula (I)

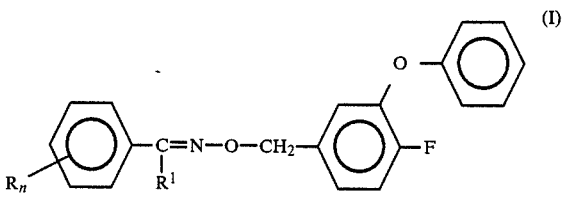

wherein R represents F, Cl, Br, I, ethoxy, methoxy or propoxy and n is an integer between 1 and 5; or R represents 3,4-methylenedioxy; and $R^1$ represents di- or trichloromethyl, fluorodichloromethyl or trifluoromethyl.

Preferred compounds are those where n=1 and R is in the 4-position on the phenyl ring.

The compounds for formula I can exist in two possible isomeric forms known as E and Z. Both isomeric forms are included in the invention.

The results of tests of insecticidal activity indicate that one isomeric form has significantly greater activity than the other.

The more active isomers of compounds of the formula (I) are distinguished by a powerful insecticidal and acaridical activity. In particular the compounds show powerful activity against cotton bud worm (*Heliothis punctigera*), an important agricultural pest.

The invention also provides methods for the production of the compounds of the formula I. One method, which is similar to that described in our copending Australian Patent Application No. 83103/82, involves reacting the appropriately substituted ketone or oxime of formula II

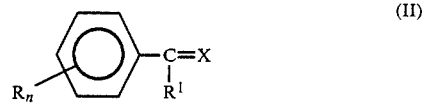

wherein R, n and $R^1$ are as defined above, and X is=O with O-(4-fluoro-3-phenoxybenzyl)-hydroxylamine hydrochloride.

This reacton is relatively slow but in some instances may be appreciably accelerated by using temperatures above room temperature. In general the reaction is conveniently carried out by stirring the reactants at the selected temperature and at atmospheric pressure.

Another method, in accordance with the invention, involves reacting the appropriately substituted oxime (formula II; X is =NOH) with 4-fluoro-3-phenoxybenzyl bromide.

The O-(4-fluoro-3-phenoxybenzyl)hydroxylamine hydrochloride can be synthesised from N-hydroxyphthalimide, 4-fluoro-3-phenoxybenzyl bromide, n-butylamine and HCl by the method of Kaztreiner, Szilagyi, Kosary and Huszti described in *Acta Chemica Academiae Scientarum Hungaricae*, 1975, 80, 167-180.

In some compounds the inactive isomer can be partly converted to the active isomer by gently heating it in a polar solvent, e.g. methanol. The isomers can be separated by any conventional method, e.g., high performance liquid chromatography (HPLC).

The active compounds are well tolerated by plants, have a favourable level of toxicity to warm-blooded animals, and can be used for combating arthropod pests, especially insects or acarids, which are encountered in agriculture, in veterinary practice, in forestry, in the protection of stored products and of materials, and in the hygiene field. They are active against normally sensitive and resistant species and against all or some stages of development. The abovementioned pests include *Lucilia cuprina*, *Blatella germanica*, and *Heliothis punctigera*.

The present invention also provides arthropodicial compositions containing as active ingredients a compound of the present invention.

The present invention also provides a method of combating anthropods (especially insects or acarids) which comprises applying to the arthropods, or to a habitat thereof, a compound of the present invention alone or in the form of a composition containing as active ingredient a compound of the present invention.

The present invention also provides a method of freeing or protecting domesticated animals from parasitical insects or acarids which comprises applying to said animals a compound according to the present invention, or a composition containing such a compound as the active ingredient.

In the compositions of this invention, the active compounds are converted into such customary formulations as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, and coating compositions for use on seed, as well as ULV cold mist and warm mist formulations.

These formulations may be produced in known manner, for example by mixing the active compounds with extenders, i.e., liquid or liquefied gaseous or solid diluents or carriers, optionally with the use of surface-active agents, i.e., emulsifying agents and/or dispersing agents and/or foam-forming agents. Where water is used as an extender, auxiliary solvents, such as for example, organic solvents, can also be used.

Examples of suitable liquid diluents or carriers, especially solvents, are aromatic hydrocarbons, such as xylene, toluene or alkyl naphthalenes, chlorinated aromatic or chlorinated aliphatic hydrocarbons, such as chlorobenzenes, chloroethylenes or methylene chloride; aliphatic or alicyclic hydrocarbons, such as cyclohexane or paraffins, for example mineral oil fractions; alcohols, such as butanol or glycol, as well as their ethers; and esters, ketones, such as acetone, methyl ethyl ketone, methyl isobutyl ketone or cyclohexanone; and strongly polar solvents, such as dimethylformamide and dimethyl sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

Examples of solid carriers are ground natural minerals, such as kaolins, clays, talc, chalk, quartz, attapulgite, montmorillonite or diatomaceous earth; and ground synthetic minerals, such as highly-dispersed silicic acid, alumina and silicates. As solid carriers for granules there may be used crushed and fractionated natural rocks such as calcite, marble, pumice, sepiolite and dolomite; as well as synthetic granules of inorganic and organic meals, and granules of organic material such as sawdust, coconut shells, maize cobs and tobacco stalks.

Examples of emulsifying and/or foam-forming agents are non-ionic and anionic emulsifiers, such as polyoxyethylene-fatty acid esters, polyoxy ethylene-fatty alcohol ethers, for example alkylaryl polyglycol ethers, alkyl sulphonates, alkyl sulphates, aryl sulphonates, as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is also possible to use colorants such as inorganic pigments, for example iron oxide, titanium oxide and Prussian Blue, and organic dyestuffs, such as alizarin dyestuffs, azo dyestuffs or metal phthalocyanine dyestuffs.

The formulations in general will contain from 0.1 to 99 percent by weight of active compound, preferably from 0.5 to 90 percent by weight.

The active compounds according to the invention may be used in the form of formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The active compounds according to the invention are also suitable for combating ectoparasites and endoparasites in the field of veterinary medicine. The compounds may be used in a known manner, such as orally in the form of, for example, tablets, capsules, drenches and granules; dermally by means of, for example, dipping, spraying, pouring-on, spotting-on and powdering.

The compounds may be employed either as the sole toxic agent in compositions such as those described above, or in combination with other insecticides such as pyrethrum, rotenone, or with fungicidal or bactericidal agents, to provide compositions useful for household and agricultural dusts and sprays, textile coating and impregnation, and the like.

In particular, the compounds of the invention may be advantageously combined with other substances which have a synergistic or potentiating action. Generally such substances are of the class of microsomal oxidase inhibitors, i.e., they inhibit the detoxification of insecticides in insects produced by the action of oxidative enzymes. Typical substances of this type are the pyrethrin synergists of which the following are examples:

[2-(2-butoxyethoxy)ethoxy]-4,5-methylenedioxy-2-propyltoluene (Piperonyl butoxide), 3-hexyl-5(3,4-methylenedioxyphenyl)-2-cyclohexanone (Piperonyl cyclonene), 2-(3,4-methylenedioxy-phenoxy)-3,6,9-trioxaundecane (Sesoxane or Sesamex), 1,2-(methylenedioxy)-4-[2(octylsulfinyl)propyl]benzene (Sulfoxide), dipropyl-5,6,7,8-tetrahydro-7-methylnaphtho-[2,3-d], 3-dioxole-5,6-dicarboxylate (n-Propyl isome), as well as propynyl ethers, propynyl oximes, propynyl carbamates and propynyl phosphonates, and S,S,S-tributyl-phosphorotrithioates. ("Sesoxane", "Sesamex" and "Sulphoxide" are Registered Trade Marks).

Piperonyl butoxide is particularly useful as a potentiator. The amount of piperonyl butoxide used may vary from 1/100th to fifty times the weight of the compound I the preferred range being from about 1/100th to five parts by weight. 'Sesamex' also is a useful potentiator in similar amounts.

Examples of formulations in accordance with the invention are as follows: (parts are by weight):

Dusts

The following substances are used to produce (a) a 5% dust and (b) a 2% dust:

(a)

5 parts of active substance,
95 parts of talcum;

(b)

2 parts of active substance,
1 part of highly dispersed silicic acid,
97 parts of talcum.

The active substance is mixed and ground with the carriers.

Granulates

The following ingredients are used to produce a 5% granulate:

5 parts of active substance,
0.25 part of epichlorohydrin,
0.25 parts of cetyl polyglycol ether, 3.50 parts of polyethylene glycol,
91 parts of kaolin The active substance is mixed with epichlorohydrin and dissolved with 6 parts of acetone, the polyethylene glycol and cetyl polyglycol ether are then added. The solution obtained is sprayed onto kaolin and the acetone is evaporated off in vacuo.

Wettable powders

The following constituents are used to produce (a) 1 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance,
4.5 parts of calcium lignin sulphonate,
1.9 parts of chalk/hydroxyethyl cellulose mixture (1:1),
1.5 parts of sodium dibutyl-naphthalene sulphonate,
19.5 parts of silicic acid,
19.5 parts of chalk,
28.1 parts of kaolin;

(c)

25 parts of active substance,
2.5 parts of isooctylphenoxy-polyoxyethylene ethanol,
1.7 parts of chalk/hydroxyethyl cellulose mixture (1:1),
8.3 parts of sodium aluminium silicate,
16.5 parts of keiselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin, The active substance is intimately mixed in suitable mixers with the additives, and the mixture is then ground in the appropriate mills and rollers to obtain wettable powders which can be diluted with water to give suspensions of the desired concentration.

Emulsifiable Concentrates

The following substances are used to produce (a) a 10%, (b) a 25%, and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;

(c)

50 parts of active substance,
4.2 parts of tributylphenol-polyglycol ether,
5.8 parts of calcium-dodecylbenzenesulphonate,
20 parts of cyclohexanone,
20 parts of xylene.

Emulsions of the required concentration can be prepared from these concentrates by dilution with water.

Sprays

The following constituents are used to produce (a) a 5% spray, (b) a 95% spray, and (c) a synergised 4% spray (a)

5 parts of active substance,
1 part of epichlorohydrin,
94 parts of ligroin (boiling limits 160°–190° C.);

(b)

95 parts of active substance,
5 parts of epichlorohydrin;

(c)

4 parts of active substance,
1 part of piperonyl butoxide,
79 parts of deodorised kerosene,
16 parts of alkylated naphthalene.

The preparation and properties of the compounds of the invention are illustrated by the following specific examples. It should be noted, of course, that these examples are intended to be illustrative of the methods and procedures utilized in preparing the compounds and that they are not intended to be restrictive or to be regarded as embodying the only way in which the compounds can be formed and recovered.

All temperatures are °C.

The O-(4-fluoro-3-phenoxybenzyl)-hydroxylamine hydrochloride used was prepared as follows:

(a) N-(4-fluoro-3-phenoxybenzyloxy)phthalimide

N-hydroxyphthalimide (2.19, 0.018 mole) was dissolved in a mixture of dry dimethoxyethane (15 ml) and dry dimethyl sulphoxide (4 ml). The clear yellow solution was cooled to 25° and potassium carbonate (1.24 g, 0.009 mol) was added. A red suspension resulted. 4-Fluoro-3-phenoxybenzyl bromide (5 g, 0.018 mol) was added dropwise over 5h at 22°–28°. The reaction mixture was stirred at room temperature overnight, after which most of the dimethoxyethane was removed in vacuo, and the solution then quenched by pouring into dilute hydrochloric acid (100 ml 1%). The resulting slurry was filtered, and the crystals washed with distilled water and dried in vacuo to give N-(4-fluoro-3-phenoxybenzyloxy)phthalimide as white crystals (6.4 g), (98%), m.p. 88.2°.

Analysis: Found C, 69.6; H, 4.0; F, 5.3; N, 3.9%. $C_{21}H_{14}FNO_4$ requires C, 69.4; H, 3.9; F, 5.2; N, 3.9%.

(b) O-(4-fluoro-3-phenoxybenzyl)hydroxylamine hydrochloride

N-(4-fluoro-3-phenoxybenzyloxy)phthalimide 5 g, 14 mmol), n-butylamine (1.13 g, 15 mmol) and absolute ethanol (3 ml) were placed in a dry flask under a nitrogen atmosphere. This reaction mixture was stirred at 60°–75° for 1.5 hours, cooled and adjusted to pH 3 using dry hydrogen chloride gas. The solution was concentrated to 10 ml and poured into dry ether. The resulting white precipitate was filtered off and recrystallized from petroleum spirit (40°–60°)/dichloromethane to give 3.2 g (87%) of a white solid, m.p. 149.3°.

Analysis: Found: C, 58.1; H, 5.1; Cl, 12.9; F, 7.0; N, 5.3%. $C_{13}H_{13}Cl\,FNO_2$ requires C, 57.9; H, 4.9; Cl, 13.2; F, 7.0; N, 5.2%).

Oxime ether preparation - Method 1

Equimolar quantities of the ketone and the O-(4-fluoro-3-phenoxybenzyl)hydroxylamine hydrochloride were dissolved in dry methanol (2.0 1/mol) and stirred at 10°–50° C. The reaction was monitored by thin layer or high pressure liquid chromatography and stopped when a satisfactory yield of product had been formed. Where the product was crystalline, it was isolated by filtration and purified by recrystallization. For oily products the methanol was removed in vacuo and the residue chromatographed on silica gel to yield the oxime-O-ether.

Oxime ether preparation - Method 2

In an inert gas atmosphere sodium hydride (1.1 mole, 50% suspension in oil) was washed free of oil with petroleum spirit (30°–40° C.), dried in vacuo and suspended in dry acetonitrile (1500 ml). To the stirred suspension was added, dropwise a solution of the oxime (1.0 mole) in dry acetonitrile (500 ml). After 1 hour at room temperature a solution of 4-fluoro-3-phenoxybenzylbromide (1.005 mole) in dry acetonitrile (500 ml) was also added dropwise. The reaction was stirred at room temperature and followed by thin layer or high performance liquid chromatography. The reaction was stopped and the reaction mixture worked up when a satisfactory yield of product had been formed. The precipitate was removed by filtration, the filtrate evaporated at 50° C. in vacuo and residue purified either by recrystallization or by chromatography on silica gel to yield the desired oxime-O-ether.

Method 1 was used to make the oxime ether compounds of the following Examples 1, 2 and 3.

EXAMPLE 1

Dichloromethyl(4-ethoxyphenyl)methanone-O-(4-fluoro-3-phenoxybenzyl)-oxime (E and Z isomers)

NMR Spectral analysis indicated that the product was a 1:1 mixture of E and Z isomers. The isomers were separated using high-performance liquid chromatography.

(a) E-isomer:
Analysis: Found: C, 61.6; H, 4.6; Cl, 15.6; F, 4.6; N, 3.2%. $C_{23}H_{20}Cl_2FNO_3$ requires C, 61.6; H, 4.5; Cl, 15.8; F, 4.2; N, 3.1%.

(b) Z-isomer:
Analysis: Found: C, 61.8; H, 4.7; Cl, 16.3; F, 4.4; N, 3.3. $C_{23}H_{20}Cl_2FNO_3$ requires C, 61.6; H, 4.5; Cl, 15.8; F, 4.2; N, 3.1%.

EXAMPLE 2

Dichloromethyl (4-chlorophenyl)methanone-O(4-fluoro-3-phenoxybenzyl)-oxime (E and Z isomers)

NMR spectral analysis indicated that the product was a 1:3 mixture of E and Z isomers. The isomers were separated using high performance liquid chromatography.

(a) E isomer m.p. 50.6° C.
Analysis: Found C, 57.5; H, 3.3; Cl, 23.8; F, 4.3; N, 2.9%. $C_{21}H_{15}Cl_3F\,NO_2$ requires C, 57.5; H, 3.5; Cl, 24.2; F, 4.3; N, 3.2%.

(b) Z isomer
Analysis: Found C, 57.6; H, 3.4; Cl, 24.4; F, 4.1; N, 2.9%. $C_{21}H_{15}Cl_3\,F\,NO_2$ requires C, 57.5; H, 3.5; Cl, 24.2; F, 4.3; N, 3.2%.

EXAMPLE 3

Trichloromethyl (4-ethoxyphenyl)methanone-O-(4-fluoro-3-phenoxybenzyl)-oxime

NMR spectral analysis indicated that there was only one isomer formed. The product was purified by high performance liquid chromatography.

Analysis: Found C, 58.3; H, 4.1; Cl, 21.3; F, 3.8; N, 3.2%. $C_{23}H_{19}Cl_3\,F\,NO_3$ requires C, 57.2; H, 4.0; Cl, 22.0; F, 3.9; N, 2.9%.

The use of Preparation Method 2 is shown in the following Example.

EXAMPLE 4

(a) Trifluoromethyl(3,4-methylenedioxyphenyl)methanone

4-Bromo-1,2-methylenedioxybenzene (4.02 g, 0.020 mole) was dissolved in dry diethylether (100 ml) and cooled to −30° C. under a dry argon atmosphere. At −30° C. to −40° C. n-butyllithium (12 ml, 0.002 mole; 1.85 molar solution in n-hexane) were added with stirring over 15 minutes. After 50 minutes at −30° C. the mixture was cooled to −50° C. and the solution of N-trifluoroacetyl piperidine (3.62 g, 0.020 mole) in dry ether (20 ml) was added over 5 minutes. After 45 minutes at −50° C. the reaction mixture was warmed up to −40° C. for 30 minutes, and to room temperature over another 30 minutes. Saturated aqueous ammonium chloride (25 ml) was added with vigorous stirring. The layers were separated and the organic top layer washed with 10% aqueous ammonium chloride (3×50 ml) and dried over anhydrous sodium sulfate. After filtration and removal of the ether under reduced pressure the residual liquid was distilled in vacuo to give trifluoromethyl (3,4-methylenedioxyphenyl)-methanone (2.2 g), (50.4%) b.p. 60° C./0.2 mm Hg.

(b) Trifluoromethyl(3,4-methylenedioxyphenyl)methanone oxime

Trifluoromethyl(3,4-methylenedioxyphenyl) methanone (1.46 g, 0.0067 mole), hydroxylamine hydrochloride (1.06 g), 0.015 mole) and sodium acetate (0.86 g, 0.010 mole) were dissolved in a mixture of methanol (4 ml) and water (4 ml) and heated to reflux for 4.5 hours. After cooling to room temperature, water (10 ml) was added and the mixture extracted with ether (3×15 ml). The combined extracts were washed with water (20 ml) and brine (20 ml) and dried over anhydrous sodium sulfate. After filtration and removal of the solvent in vacuo the residue was recrystallized from a mixture of dichloromethane and petroleum spirit (40°–60° C.) to give trifluoromethyl(3,4-methylenedioxyphenyl)methanone-oxime (1.2 g), (76.9%) m.p. 96.0° C.

(c) Trifluoromethyl(3,4-methylenedioxyphenyl)methanone-O-(4-fluoro-3-phenoxybenzyl)-oxime Preparation Method 2 was used to make the title compound from trifluoromethyl(3,4-methylenedioxyphenyl) methanone oxime. NMR spectral analysis indicated that there was only one isomer formed. The product was purified by high performance liquid chromatography.

Analysis: Found C, 61.0; H, 3.5; F, 17.3; N, 3.6%. $C_{22}H_{15}F_4NO_4$ requires C, 61.0; H, 3.5; F, 17.5; N, 3.2%.

EXAMPLE 5

Insecticidal activity was investigated against blowfly, *Lucilia cuprina*. The method used was as follows:

(a) The compounds were tested for activity against a susceptible strain which had been collected in the field.

The test compound was applied in acetone solution, 0.5 μl dispensed with a Drummond micropipette to the dorsum of the thorax of 2-3 day old females. Adult flies were fed on water and sugar-only and maintained at 25° C. and 60-70% RH. The mortalities were determined after 48 hours. Moribund flies were regarded as dead. The $LD_{50}$ values, in terms of concentration, were interpolated from a probit/log dose graph using a computer program.

(b) Potentiation

The compound was also tested on the insects described above in conjunction with the potentiator piperonyl butoxide by pretreating each insect with 1 μl of a 2% solution of the potentiator in acetone.

The mortalities were counted at 48 hours after treatment and compared with acetone and acetone/potentiator controls.

The $LD_{50}$ value was determined as described above.

About the same levels of potentiation were obtained when piperonyl butoxide was replaced by an equal amount of 'Sesamex'.

Using the above-described techniques, $LD_{50}$ values were determined on each of the compounds listed in Table 1.

Comparative tests were also carried out on a commercially available synthetic pyrethroid insecticide "Permethrin", i.e., the 3'-phenoxybenzyl ester of 3-(2',2'-dichlorovinyl)-2,2-dimethylcyclopropane carboxylic acid, (mixture of 60:40 trans:cis isomers).

For ease of comparison the results obtained are expressed in Table 1, in terms of a "potency index" given by $$\text{Potency Index} = \frac{LD_{50} \text{ for Permethrin}}{LD_{50} \text{ for test compound}} \times \frac{100}{1}$$

The $LD_{50}$ for permethrin was determined concurrently with the $LD_{50}$ for the test compound.

EXAMPLE 6

Insecticidal activity against the German cockroach (*Blatella germanica*) was determined using the following method:

The compound under test was applied in acetone solution at a range of concentrations. 0.5 μl was dispensed with a Drummond micropipette to the ventral thorax of adult cockroaches. The mortalities were determined after 48 hours. Moribund cockroaches were regarded as dead. The $LD_{50}$ values in terms of concentration were determined by probit analysis of the mortality/concentration data and converted to Potency Index values.

The results are shown in Table 1.

EXAMPLE 7

Insecticidal activity against the cotton pest *Heliothis punctigera* was determined using the following method:

The compound under test was applied in acetone solution at a range of concentrations. 0.5 μl was dispensed with a Drummond micropipette to the dorsal surface of 3rd instar larvae. Each larva was held in a separate container and was fed on spinach and maintained at 25° C. and 60-70% RH. The mortalities were determined after 48 hours. Moribund larvae were regarded as dead. The $LD_{50}$ values in terms of concentration were determined by a probit analysis of the mortality/concentration data and converted to Potency Index values.

The results are given in Table 1.

TABLE 1

| Compound of Example No. | INSECTICIDAL ACTIVITY Potency Index Against | | | |
| --- | --- | --- | --- | --- |
| | *Lucillia cuprina* (alone) | *Lucillia cuprina* (+potent.) | *Blatella germanica* | *Heliothis punctigera* |
| Permethrin | 100 | 100 | 100 | 100 |
| 1(a) (E isomer) | 140 | 21 | 1400 | 985 |
| 1(b) (Z isomer) | 71 | 72 | 940 | 640 |
| 2(a) (E isomer) | 6 | 4 | 54 | |
| 2(b) (Z isomer) | 10 | 17 | 12 | |
| 3 | 17 | 8 | <8 | |
| 4 | 4 | 2 | <8 | |

I claim:
1. A compound of formula (I)

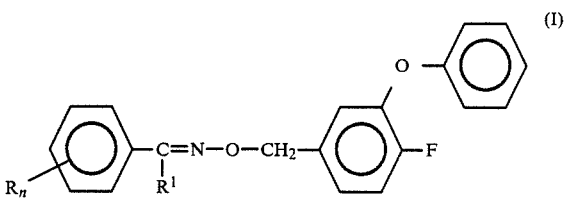

wherein R represents F, Cl, Br, I, ethoxy, methoxy or propoxy and n is an integer between 1 and 5; or R represents 3,4-methlenedioxy; and $R^1$ represents di- or trichloromethyl, fluorodichloromethyl or trifluoromethyl and a E or Z isomer thereof or a mixture of these isomers.

2. A compound as claimed in claim 1, characterized in that n is 1 and R is in the 4-position on the phenyl ring.

3. Trichloromethyl (4-ethoxyphenyl)methanone-O-(4-fluoro-3-phenoxybenzyl)-oxime.

4. Trifluoromethyl (3,4-methylenedioxyphenyl)methanone-O-(4-fluoro-3-phenoxybenzyl)-oxime.

5. An arthropodicidal composition which comprises as an active ingredient an arthropodically effective amount of a compound of the formula (I) as claimed in claim 1 in admixture with a veterinarian acceptable diluent or carrier.

6. A composition as claimed in claim 5, which also includes at least one substance which has a synergistic or intensifying effect on pyrethroids and which is a microsomal oxidase inhibitor.

7. A composition as claimed in claim 6, wherein the substance is selected from propynyl ethers, propynyl oximes, propynyl carbamates, propynyl phosphonates, S,S,S-tributylphosphorotrithioates, [2-(2-butoxyethoxy)ethoxy]-4,5-methylenedioxy-2-propyltoluene (Piperonyl butoxide), 3-hexyl-5(3,4-methylenedioxyphenyl)-2-cyclohexanone (Piperonyl cyclonene), 2-(3,4-methylenedioxy-phenoxy)-3,6,9-trioxaundecane (Sesoxane or Sesamex), 1,2-(methylenedioxy)-4-[2-(octylsulfinyl)-propyl]-benzene (Sulfoxide), and dipropyl-5,6,7,8-tetrahydro-7-methylnaphtho[2,3-d]3-dioxole-5,6-dicarboxylate (n-Propyl isome).

8. A composition as claimed in claim 7, wherein the substance is present in the composition in an amount of from 1/100th to fifty times the weight of the compound of formula (I).

9. A composition as claimed in claim 7, wherein the amount is from 1/100th to five times the weight of the compound of formula (I).

10. A method of combating arthropods which comprises applying to the anthropods, or to a habitat thereof, an effective amount of the composition of claim 5.

11. A method of freeing or protecting domesticated animals from parasitical insects or acarids which comprises applying to said animals an effective amount of the composition of claim 5.

12. Dichloromethyl(4-ethoxyphenyl)methanone-O-(4-fluoro-3-phenoxybenzyl)-oxime or its E or Z isomer, or a mixture of these isomers.

13. Dichloromethyl(4-chlorophenyl)methanone-O-(4-fluoro-3-phenyxoybenzyl)-oxime or its E or Z isomer, or a mixture of these isomers.

* * * * *